US00PP21876P2

(12) United States Plant Patent
Hurd

(10) Patent No.: US PP21,876 P2
(45) Date of Patent: Apr. 19, 2011

(54) ***DIANTHUS* PLANT NAMED 'COCONUT PUNCH'**

(50) Latin Name: ***Dianthus* hybrid**
Varietal Denomination: Coconut Punch

(75) Inventor: Kevin Hurd, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 12/462,744

(22) Filed: Aug. 7, 2009

(51) Int. Cl.
*A01H 5/00* (2006.01)

(52) U.S. Cl. ..... Plt./272

(58) Field of Classification Search ..... Plt./272
See application file for complete search history.

*Primary Examiner* — Susan B McCormick Ewoldt

(57) ABSTRACT

The new and distinct cultivar of perennial Carnation or Pinks, *Dianthus* plant named 'Coconut Punch' with fragrant highly double flowers, petals with a reddish purple margin zone and petal limb base, with highly contrasting white petal center and thin white rim. *Dianthus* 'Coconut Punch' is tolerant of high temperatures and resists center die out.

2 Drawing Sheets

Botanical denomination: *Dianthus* hybrid.
Cultivar designation: 'Coconut Punch'.

BACKGROUND OF THE INVENTION

The present invention relates to the new and distinct cultivar of *Dianthus* or Pinks from the genus *Dianthus* and given the cultivar name 'Coconut Punch'. The new plant was the result of an intentional cross in May of 2006 by Kevin A. Hurd between 'Double Spotty' U.S. Plant Pat. No. 13,884 as the seed parent and 'Red Dwarf' U.S. Plant Pat. 14,437 (more often known as 'Eastern Star') as the pollen parent. The new hybrid was first isolated from trials at a nursery in Zeeland, Mich. during the summer of 2007. *Dianthus* 'Coconut Punch' has been asexually propagated at the same nursery in Zeeland, Mich. using traditional shoot tip cutting procedures and found to reproduce plants that are identical and exhibit all the characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Double flowers with high petal counts.
2. Highly contrasting light and dark floral pattern.
3. High heat tolerance.
4. Floriferous habit.
5. Vigorous growth and excellent habit.
6. Compact, distinctly blue-green foliage.

Cultiver Comparison Table

| Cultiver | Flower color | Flower pattern | Flower size |
|---|---|---|---|
| 'Apple Slice' application Ser. No. 12/462,743 | pink | dark wine edge and rim | 4.5 cm |

-continued

Cultiver Comparison Table

| | | | |
|---|---|---|---|
| 'Black Cherry Wild' application Ser. No. 12/462,742 | burgundy | solid | 4.0 cm |
| 'Coconut Punch' application Ser. No. 12/462,744 | white | burgundy edge with white rim | 3.5 cm |
| 'Double Spotty' U.S. Plant Pat. No. 13,884 | burgundy | white picotee edge and white spots | 4.0 cm |
| 'Dragon Fruit' application Ser. No. 12/462,745 | fuchsia pink | red jagged purple bar | 3.5 cm |
| 'Pomegranate Kiss' application Ser. No. 12/462,746 | burgundy | irregular pink splashing on margin or center | 3.2 cm |
| 'Cranberry Ice' U.S. Plant Pat. No. 18,342 | pink | dark wine edge and rim | 3.3 cm |
| 'Devon Siskin' U.S. Plant Pat. No. 14,377 | light pink | magenta edge with burgundy base | 4.0 cm |
| 'Feuerhexe' (not patented) | pink | solid | 4.0 cm |
| 'Devon Xera' U.S. Plant Pat. No. 14,895 | red | crimson eye | 3.0 cm |
| Red Dwarf' U.S. Plant Pat. No. 14,437 | red | crimson eye | 3.5 cm |
| 'Sangria Splash' application Ser. No. 12/462,741 | fuchsia pink | crimson ring with pink splashing and center | 3.0 cm |
| 'Spangled Star' U.S. Plant Pat. No. 13029 | scarlet red | small white spots and white picotee edge | 4.0 cm |

| Cultiver | Petal margin | Petal # | Plant height in flower |
|---|---|---|---|
| 'Apple Slice' application Ser. No. 12/462,743 | dark wine margin | 20 to 24 | 22 cm |
| 'Black Cherry Wild' application Ser. No. 12/462,742 | light rose margin | 16 to 20 | 22 cm |
| 'Coconut Punch' | reddish | 14 to | 28 cm |

-continued

| Cultiver Comparison Table | | | |
|---|---|---|---|
| application Ser. No. 12/462,744 | purple margin | 30 | |
| 'Double Spotty' U.S. Plant Pat. No. 13,884 | white | 15 to 20 | 17 to 30 cm |
| 'Dragon Fruit' application Ser. No. 12/462,745 | self | 14 to 22 | 20 cm |
| 'Pomegranate Kiss' application Ser. No. 12/462,746 | irregular pink splashing | 16 to 22 | 16 cm |
| 'Cranberry Ice' U.S. Plant Pat. No. 18,342 | dark wine margin | 5 | 20 to 25 cm |
| 'Devon Siskin' U.S. Plant Pat. No. 14,377 | magenta edge | 5 | 10 cm |
| 'Feuerhexe' (not patented) | self | 5 | 10 to 12 cm |
| 'Devon Xera' U.S. Plant Pat. No. 14,895 | self | 5 | 15 to 20 cm |
| Red Dwarf' U.S. Plant Pat. No. 14,437 | self | 5 | 20 to 25 cm |
| 'Sangria Splash' application Ser. No. 12/462,741 | crimson with pink splashing | 5 | 30 cm |
| 'Spangled Star' U.S. Plant Pat. No. 13029 | white picotee edge | 5 | 17 to 22 cm |

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
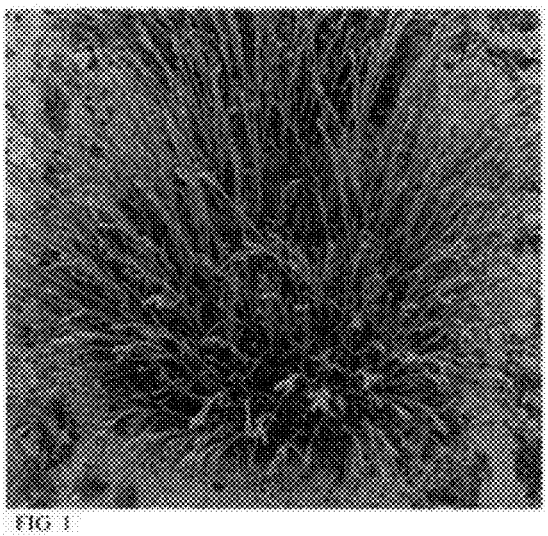
FIG. 1 shows the new plant at two-years old in flower.
Figure 2:
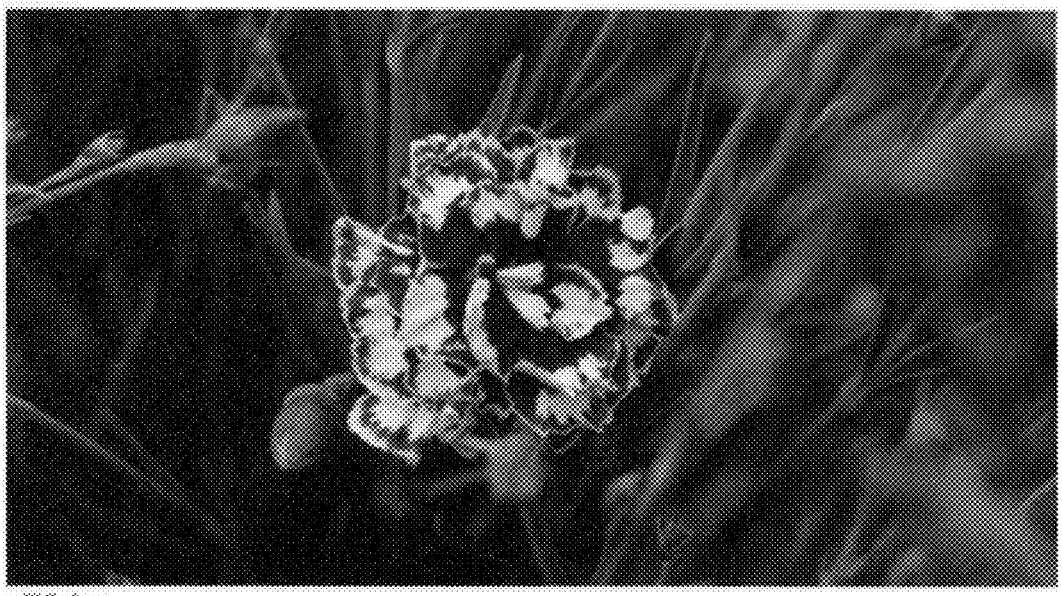
FIG. 2 shows a close-up of the flower and bud.
Figure 3:
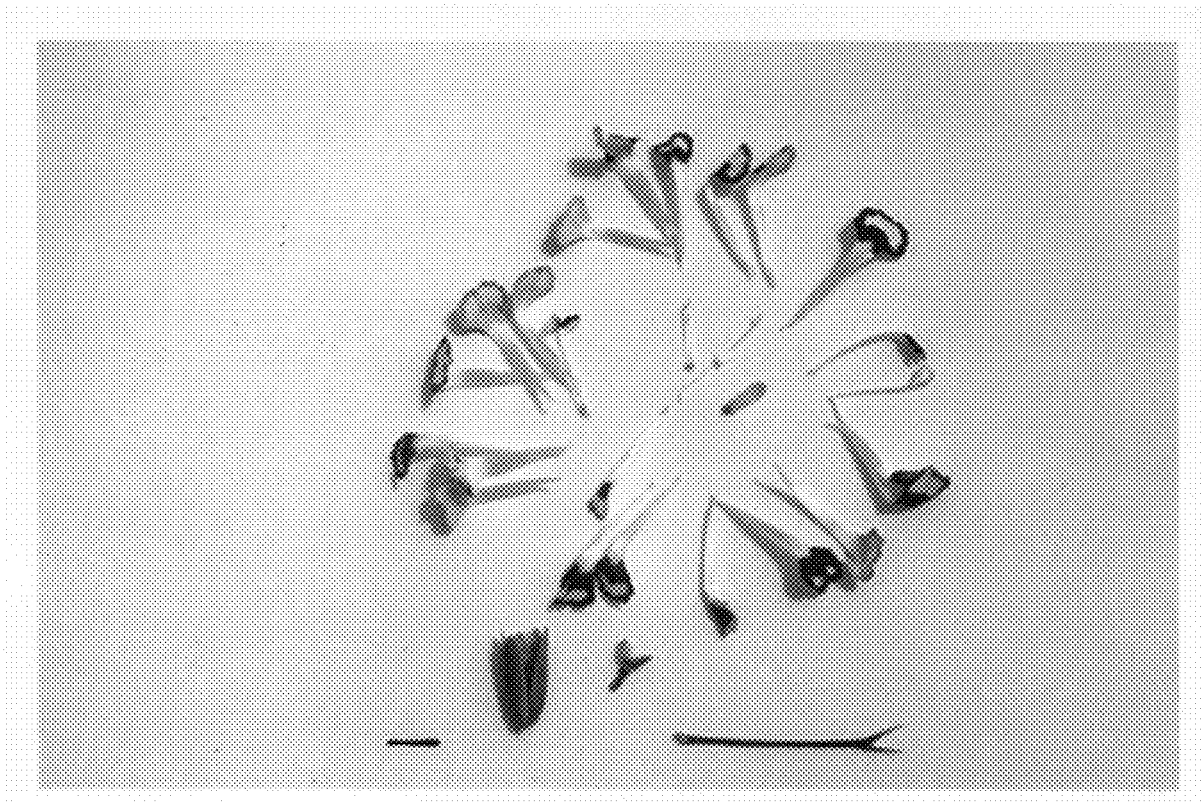
FIG. 3 shows the dissected flower of the new plant together with capsule and seeds.

The following detailed description of the new plant is based on observations of several two-year old plants in open-field, full-sun conditions in Zeeland, Mich. with supplemental watering, light additions of fertilizer and free of other plant growth regulators. All color usage is in reference to the 2001 edition of The Royal Horticultural Colour Chart except where common dictionary terms are used.

Botanical classification: *Dianthus* hybrid;

Parentage: 'Double Spotty' (female) times 'Eastern Star' (male);

Plant description:

*Habit.*—Cespitose, herbaceous, evergreen perennial; stems proximally branched, erect; height of foliage about 18 cm and 40 cm across; about 28 cm tall in flower; Root system; fibrous.

Foliage:

Leaf type: Simple, linear, opposite, decussate, sessile, glabrous, glaucous on adaxial and abaxial; acute apex; base decurrent, adpressed along stem and somewhat perfoliate; no fragrance detected;

*Leaf dimensions.*—About 5 cm long and 3 mm wide.

*Leaf color.*—Nearest RHS 122B adaxial and abaxial sides.

*Venation.*—Finely reticulate, coloration same as that of leaf top and bottom.

*Stems.*—Erect to arching, terete, glabrous, glaucous, proximally branching at 4 to 5 nodes.

*Stem size.*—About 28 cm long and 2 mm wide at base.

*Stem color.*—Nearest RHS 122B.

*Branching.*—Numerous from lower leaf axils; about 180 per plant.

*Nodes.*—4 mm across, RHS N134A.

*Internodes.*—5.0 to 5.5 cm apart.

Inflorescence:

*Type.*—Terminal, cymose, erect.

*Flowers per stem.*—Usually 4 to 7.

*Pedicel.*—Glaucous, glabrous, terete.

*Pedicel size.*—Usually 3 to 4 cm long and 2 mm diameter.

*Pedicel color.*—Nearest RHS 122A.

Flowers:

*Type.*—Salviform, completely double, symmetrical. Dimension about 3.5 cm across and extending about 1.5 cm above calyx.

*Flower bud shape.*—Rhomboid to terete.

*Flower bud size one day prior to opening.*—About 2 cm long and 1 cm wide.

*Flower bud color.*—Glaucous, between RHS 139D and RHS 139C and with anthocyanin patches between RHS 187B and RHS N187B.

*Flower period.*—Starting early June and after a 2 week rest continuing until frost.

*Flower lasting quality.*—About one week on or off the plant.

*Flower fragrance.*—Light, sweet spicy, clove-like.

*Petals.*—14 to 30, consisting of a rounded blade or limb and a claw (enclosed completely within the calyx), obovate, apex dentate with dentations 3 to 4 mm deep, bearded with minute hairs mostly on the center of the adaxial surface, bent outwardly to nearly a ninety degree angle; reddish purple margin about 5 mm thick and at base of limb on adaxial side with white rim surrounding red margin.

*Dimension.*—Variable, to 3.2 cm long including claw and limb; larger petal limbs to 1.2 cm across and 1.0 cm long, smaller limbs to 3 mm across and 5 mm long; claws range from 1.7 cm to 2.4 cm long and 2 mm to 4 mm wide about 3 mm from limb; white rim about 1 to 2 mm wide, reddish purple margin about 3 mm thick and reddish purple at base of petal limb about 5 mm wide.

*Color.*—Adaxial limb: white rim much lighter than RHS 76D; reddish purple margin RHS 5 base of the petal limb RHS 59A going down to RHS 64C for about 1 mm before the white top of the claw much lighter than RHS 69D; abaxial limb: (showing through from adaxial side) closest to RHS 73D; claw: between RHS 145B and RHS 145C both sides.

*Calyx.*—Glabrous, glaucous, five-toothed corolla tube fused in proximal 1.0 cm; about 1.8 cm long and 0.7 cm in diameter; RHS 147D with some anthocyanin tinting between RHS 187B and RHS N187B.

*Peduncle.*—Glabrous, glaucous, terete, 22 cm long and 2 mm diameter; RHS N138D.

*Bracts.*—Two, opposite, broadly obtuse with acute apex, about 8 mm long and 7.5 mm wide; RHS N138C in the center, lighter than RHS 138D at base and margins.

*Bracteoles.*—Two, opposite, broadly obtuse with acute apex, bases joined at stem; about 6 mm long and 3 mm wide; glaucous, RHS N138C at apex and center, lighter than RHS 138D at base and margins.

*Stipules.*—None present.

*Androecium.*—Stamens 6, filaments variable in length from 1.2 to 1.8 cm long, less than 1 mm diameter; pale green lighter than RHS 11D; anther oblong to 2.2 mm long and 1 mm wide, RHS 164B; pollen rare, pollen color RHS 11D.

*Gynoecium.*—Style usually split in two above ovary, pistil 1.5 cm long and about 1 mm diameter, white, lighter than RHS 11D except for distal 5 mm which are lighter than RHS 77D; stigma between RHS 76D and RHS 75D.

*Ovary.*—Superior, spindle-shaped; 8 mm long and 3 mm wide; between RHS 145C and RHS 145 B at distal end and nearest RHS 150D at proximal end.

Seed: Seeds have not been observed.

Growth rate: Vigorous, finishing from a 3 cm liner into a 15 cm in 6 to 8 weeks;

Comparison varieties: The new plant can be compared to the varieties in the Cultivar Comparison Table. The nearest known comparison cultivar is 'Double Spotty', but the new plant has a white petal instead of the light rosy pink petal, and the petal rim is a burgundy instead of the reddish rose of 'Double Spotty'.

Disease resistance: The new plant is resistant to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct cultivar of perennial Carnation or Pinks, *Dianthus* plant named 'Coconut Punch' as herein described and illustrated, with fragrant highly double flowers, petals with a reddish purple margin zone and petal limb base, with highly contrasting white petal center and thin white rim, resistant to high temperatures and center die out, and suitable as a garden ornamental, potted plant and for cut flower arrangements.

* * * * *